United States Patent
Cano Cediel et al.

(10) Patent No.: US 8,964,174 B2
(45) Date of Patent: Feb. 24, 2015

(54) MARKING AND DEFECT RECOGNITION PROCEDURE IN PREPREG MATERIAL

(75) Inventors: Jose David Cano Cediel, Madrid (ES); Georgina Galera Cordoba, Madrid (ES)

(73) Assignee: Airbus Operations, S.L., Getafe (ES)

( * ) Notice: Subject to any disclaimer, the term of this patent is extended or adjusted under 35 U.S.C. 154(b) by 67 days.

(21) Appl. No.: 13/533,015

(22) Filed: Jun. 26, 2012

(65) Prior Publication Data

US 2013/0169956 A1   Jul. 4, 2013

(30) Foreign Application Priority Data

Jun. 28, 2011   (ES) .................. P201131084

(51) Int. Cl.
*G01N 21/00* (2006.01)
*G01N 21/89* (2006.01)
*G01N 21/88* (2006.01)

(52) U.S. Cl.
CPC ...... *G01N 21/8914* (2013.01); *G01N 2021/888* (2013.01); *G01N 21/8851* (2013.01)
USPC .................................... 356/237.1; 356/237.2

(58) Field of Classification Search
CPC .. D06H 3/16; G01N 21/8915; G01N 21/9501
See application file for complete search history.

(56) References Cited

U.S. PATENT DOCUMENTS

| | | | |
|---|---|---|---|
| 2006/0164647 A1* | 7/2006 | Shibata | 356/430 |
| 2009/0086209 A1* | 4/2009 | Uesugi et al. | 356/431 |
| 2011/0135872 A1 | 6/2011 | Michal et al. | |
| 2013/0177215 A1* | 7/2013 | Campbell et al. | 382/111 |

FOREIGN PATENT DOCUMENTS

| | | |
|---|---|---|
| DE | 20303574 | 4/2003 |
| JP | 08-184956 | 7/1996 |

* cited by examiner

*Primary Examiner* — Michael P Stafira
(74) *Attorney, Agent, or Firm* — Oblon, Spivak, McClelland, Maier & Neustadt, L.L.P.

(57) ABSTRACT

A defect recognition procedure in prepreg materials (1) draws a first transversal cross line (4b) at the beginning boundary (3b) of a defective area (2) in a prepreg material (1). A second transversal cross line (4e) at the end boundary (3e) of a defective area (2) is drawn as well. The cross lines (4b, 4e) form an angle ($\alpha$) with respect to the prepreg material (1) motion direction (5).
Each transversal cross line (4b, 4e) delimiting the beginning and the end of a defective area (2) has identification codes ($B_i$, $E_i$).

8 Claims, 3 Drawing Sheets

MARKING AND DEFECT RECOGNITION PROCEDURE IN PREPREG MATERIAL

OBJECT OF THE INVENTION

This invention discloses a procedure for marking and detecting defective areas in preimpregnated material (also called "prepreg"). It is included in the technical field of composite material manufacturing, especially for the aerospace industry.

PROBLEM TO BE SOLVED AND BACKGROUND OF THE INVENTION

Most modern aircraft and spacecraft are manufactured using composite materials with carbon fibres. There are several techniques for manufacturing composite materials, like Resin Transfer Moulding (RTM), Vacuum Assisted Resin Transfer Moulding (VARTM), Resin Infusion Moulding (RIM), Fiber Placement (FP), Automated Fiber Placement (AFP) or Automatic Tape Lying (ATL). All these techniques are well known in the state of the art.

Preimpregnated materials ("prepregs") are used in some of these techniques. When manufacturing prepreg materials sometimes defects are also created, so defective areas must be detected and registered. Prepreg manufacturers include a reference of defective areas associated to each prepreg roll. These defective areas can be controlled and scrapped when laying up using an encoder; an encoder is a device which measures the length of each prepreg material roll as it is being laid up. The prepreg manufacturer includes a defective areas list with each roll, so through the encoders' use it is possible to detect the proximity of a defective area. However, sometimes encoders are imprecise due to the fact that prepreg rolls may slip or encoders may reset; therefore, encoders' information may be wrong and some potential defective areas may be laid up on the part.

Current automatic tape laying machines include laser defect detection systems based on shade contrast. Nevertheless, the fine calibration of these defect detection systems is hardly achieved due to reflections produced by the incident light against the resin of the prepeg material. The system generates continuous false alarm situations because of these reflections. That is the reason why they are not accurate enough and are usually turned off.

This invention presents a system to overcome the mentioned drawbacks, marking failures in prepreg rolls. The object of the invention is to include transversal cross lines in the boundary of a defective area in a prepreg material. These transversal lines are marked with a non pollutant material having a chemical composition that do not contaminate the prepreg material; therefore, the marked lines mean no change of the technical features of the final product.

These marked lines allow detecting defective area in the prepreg material, avoiding their use in the parts that are going to be manufactured. The prepreg rolls having defective areas are cut and scrapped before the prepreg material is laid up with the ATL machine (or any other machine used during the manufacturing process). Therefore, a cost reduction is achieved due to the fact that manufactured parts do not include those defective areas, and the parts are not rejected when passing quality control inspections.

The state of the art shows different devices and procedures for manufacturing and supplying prepreg materials. Document WO 2008/120023 A1 discloses a method and apparatus for making thermoplastic prepregs with specific fiber orientation. Document JP 2005246631 A reveals a method for detecting different kinds of prepreg materials and apparatus thereof. However, no evidence about a procedure to recognize defective areas in prepreg materials according to the present invention has been found.

SUMMARY OF THE INVENTION

In order to achieve the objectives and to solve the aforementioned drawbacks, the invention has developed a defect recognition procedure in prepreg materials. The procedure is characterized by drawing a first transversal cross line at the beginning boundary of a defective area in a prepreg material, and drawing a second transversal cross line at the end boundary of a defective area in a prepreg material.

The cross lines form an angle with respect to the prepreg material motion direction; such angle varies from 45° to 90°.

Each first transversal cross line delimiting the beginning of a defective area has a first identification code. Similarly, and each second transversal cross line delimiting the end of a defective area has a second identification code.

According to a first embodiment, the first identification code and the second identification code are linked using alphanumeric characters. In a second embodiment, the first identification code and the second identification code are linked using graphic characters.

The lines are drawn with a non pollutant material that does not contain fluorine, neither polytetrafluoroetylene nor uncured silicone. Such lines are detected by a defect detector laser sensor integrated in a manufacturing machine.

The defect detector laser measures the loss of gain between a first signal sent by the laser (preset value) and the signal that the laser receives (current value) when such first signal rebounds against the composite material.

During the procedure, the comparison between the signal preset value and the signal current value determines whether or not there are defective areas, so: a) if the current value is set below a certain reference (for instance 30) defective areas (2) are not considered; or, b) if the current value exceeds a certain reference (for instance 100) defective areas are considered and the laser control generates a signal error, stopping the machine.

In order to facilitate a better understanding of this specification, and being an integral part thereof, a series of figures in which the object of the invention has been represented with an illustrative and not limitative manner is attached.

BRIEF DESCRIPTION OF THE DRAWINGS

The invention will be better understood from reading the following detailed description taken in conjunction with the drawings in which similar reference numbers are used to designate similar elements, and in wherein.

A list of reference numbers used on the drawings is given hereinafter: 1=prepreg material and roll where it is stored; 2=defective area; 3=boundary of a defective area; 3*b*=beginning boundary; 3*e*=end boundary; 4=transversal cross lines; 4*b*=transversal cross line at the beginning boundary; 4*e*=transversal cross line at the end boundary; 5=prepreg material motion direction; 6=uni-directional dry fibres; 7=resin film; 8=fibre and resin heating; 9=fibre and resin compaction; 10=inspection and line marking;

$B_i$=identification code at the beginning of a defective area;
$E_i$=identification code at the end of a defective area.

DETAILED DESCRIPTION

A description of the invention based on the aforementioned figures is made hereinafter.

Figure 1:
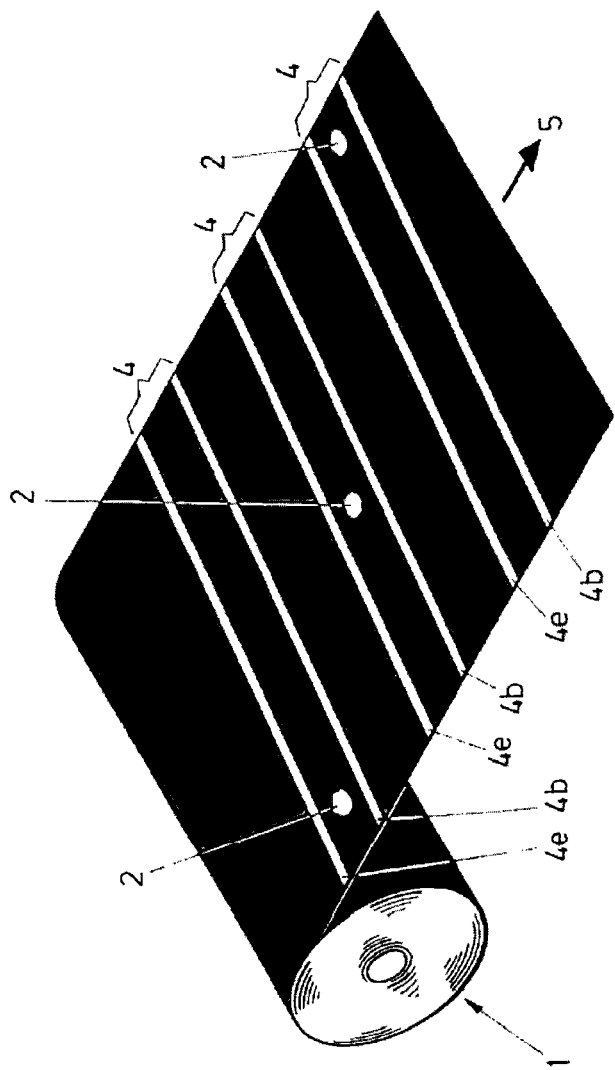
FIG. 1 is a general view of a prepreg roll with marks highlighting defective areas at such prepreg roll.

FIG. 1 shows a prepreg material roll (1) that is used for manufacturing a part; the prepreg roll (1) may feed the ATL machine or another device well known in the state of the art for manufacturing composite parts. The prepreg material (1) is moved in a motion direction (5) to feed the machine (not represented) that manufactures the parts. The prepreg material (1) might have several defective areas (2). These defective areas (2) must be avoided when manufacturing the parts; otherwise these parts will have to be rejected during the quality control process, increasing the manufacturing cost. In order to detect the defective areas (2), several transversal cross lines (4) are marked for detecting these defective areas (2). Each defective area (2) is surrounded by a first transversal cross line (4b) at the beginning of the defective area (2), and by a second transversal cross line (4e) at the end of the defective area (2). A more detailed illustration can be seen in FIG. 2.

Figure 2:
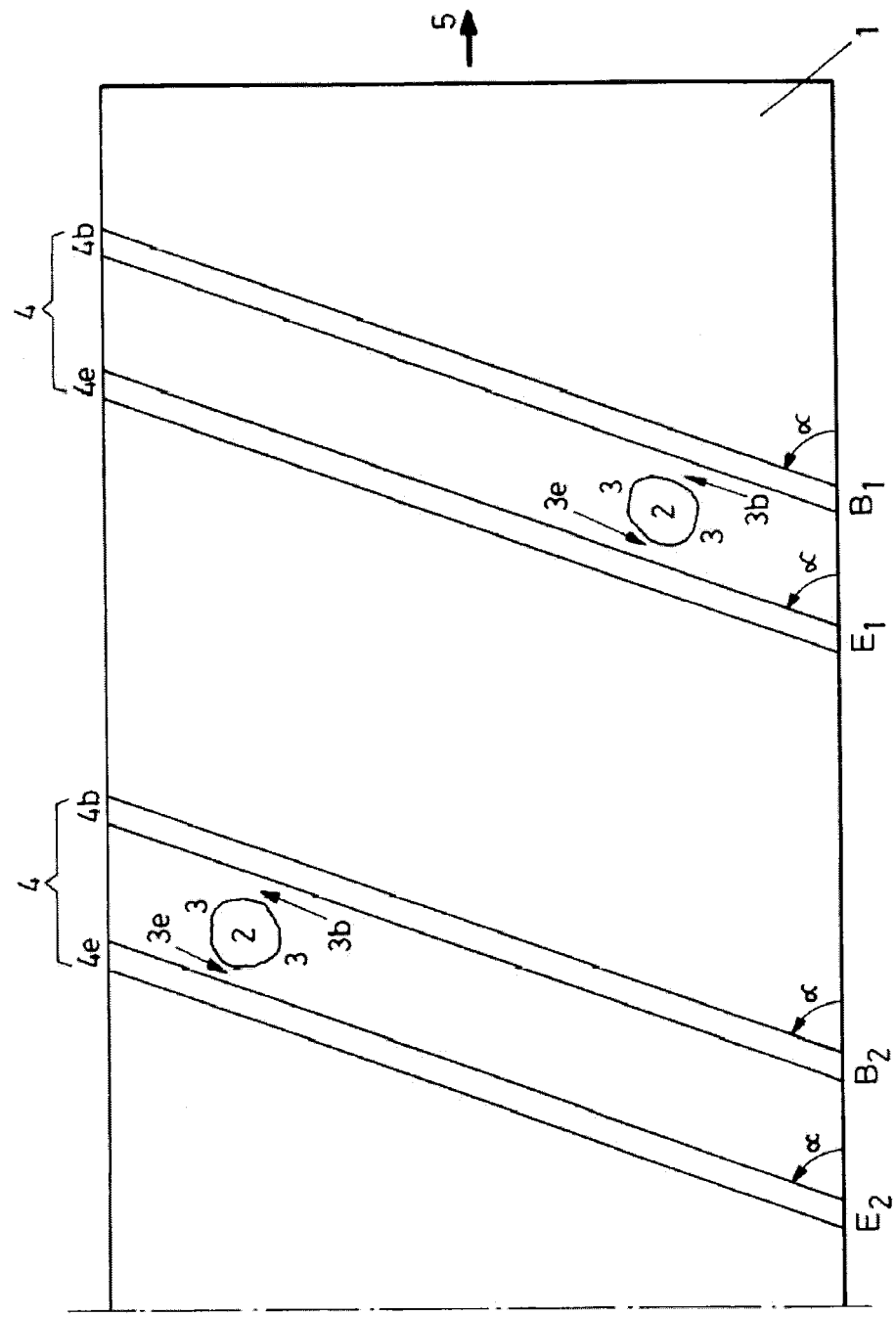
FIG. 2 shows a top view of the prepreg roll, detailing those marks.

FIG. 2 shows a top view of the prepreg roll (1), detailing the previous mentioned cross lines (4b, 4e). The defective areas (2) can be detected by their boundaries (3), having a beginning boundary (3b) and an end boundary (3e). The beginning boundary (3b) and the end boundary (3e) have been considered according to the previous mentioned motion direction (5), although other references could have been considered when defining these boundaries (3, 3b, 3e).

The cross lines (4b, 4e) form an angle ($\alpha$) with respect to the prepreg material (1) motion direction (5). Experience has shown that these lines (4b, 4e) must have some kind of inclination in order to optimize their detecting properties; sensors detecting these lines (4b, 4e) achieve a maximum detection when the mentioned angle ($\alpha$) values vary from 45° to 90°.

Due to the fact that each defective area (2) detected in the prepreg material (1) is marked with a first transversal cross line (4b) and a second transversal cross line (4e), the total number of transversal cross lines (4b, 4e) must be an even number; otherwise there will be some defective areas (2) wrongly marked. In order to increase safety conditions, each first transversal cross line (4b) delimiting the beginning of a defective area (2) has a first identification code ($B_i$). Equally, each second transversal cross line (4e) delimiting the end of a defective area (2) has a second identification code ($E_i$) as well. Both codes ($B_i$, $E_i$) are linked. There are several linking options: one of them is to use a code with alphanumeric characters. According to this option, the first defective area (2) detected in a prepreg material (1) is marked using a first transversal cross line (4b) having a code ($B_1$); the second transversal cross line (4e) delimiting the end of the first defective area (2) has a second identification code ($E_1$). Similarly the second defective area (2) detected has an identification code ($B_2$) for its first transversal cross line (4b) delimiting the beginning of the second defective area (2), and there is another identification code ($E_2$) for the second transversal cross line (4e) delimiting the end of the second defective area (2) as well. Therefore, for N defective areas (2) detected in the prepreg material (1) there are 2N identification codes: $B_1$, $E_1$, $B_2$, $E_2$, $B_3$, $E_3$, ... $B_N$, $E_N$.

A sensor (not shown) detects each identification code ($B_i$, $E_i$) included at each transversal cross line (4b, 4e). The sensor reads the first identification code ($B_i$) associated to a defective area (2), and immediately it reads the second identification code ($E_i$); in case of a malfunction when detecting any of these codes ($B_i$, $E_i$) (i.e. that one of them has not been detected) an error signal is produced, a message is shown in the machine control display and the machine stops until the operator checks the roll and the lay up process is resumed.

Other linking methods may be employed using graphic characters instead of alphanumeric ones. This means that each identification code ($B_i$, $E_i$) may be set up by graphic characters using geometric shapes (like circles, triangles, squares, and other geometric figures and their combinations). This embodiment has not been illustrated in the figures.

Figure 3:
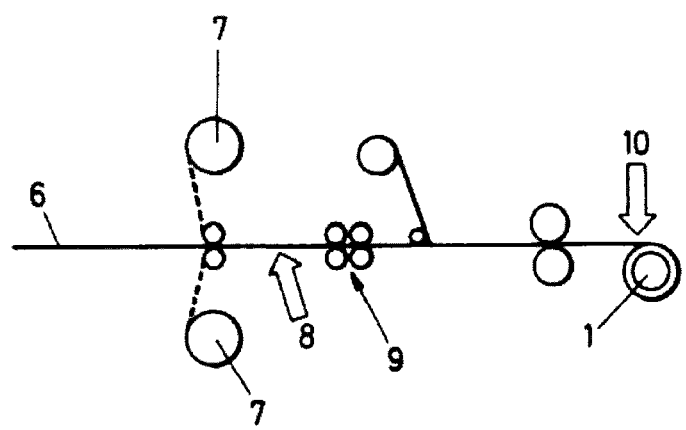
FIG. 3 is a general scheme of a prepreg manufacturing process, including the defective areas marking.

FIG. 3 represents a general scheme of a prepreg material (1) manufacturing process, including the marking of defective areas (2). Uni-directional dry fibres (6) are mixed together with resin film (7). Later on this mixture undergoes heating (8) and compaction (9) processes. Finally the prepreg material (1) is inspected and marked (10) with cross lines (4b, 4e) when defective areas (2) are detected. After the inspection and marking process (10), the prepreg material (1) is stored in rolls.

The cross lines (4b, 4e) are marked with a non pollutant material that do not contaminate the prepreg material (1). Typical waste material that can damage composite materials are fluorine, polytetrafluoroetylene (PTFE, Teflon®) and uncured silicone waste; therefore, the marking material cannot contain any of these substances.

The cross lines (4b, 4e) also have such optical characteristics of refraction that enables the possibility to be detected with the standard ATL machine defect detector laser. This defect detector laser measures the loss of gain between a first signal sent by the laser (called preset value) and the signal that the laser receives (current value) when such first signal rebounds against the composite material (1). For detecting defective areas (2), the comparison between the signal preset value and the signal current value determines whether or not there are defectives areas (2). If the current value is set below a certain reference (for instance 30) defective areas (2) are not considered; nevertheless, if the current value exceeds a certain reference (for instance 100) defective areas (2) are considered and the laser control generates a signal error, stopping the machine. Thus, the defective areas (2) are discarded preventing them from being used in the manufacture of new parts.

The invention claimed is:

1. A defect recognition procedure in prepreg materials, comprising:
   drawing a first transversal cross line at the beginning boundary of a defective area in a prepreg material and drawing a second transversal cross line at the end boundary of a defective area in a prepreg material,
   wherein the cross lines form an angle ($\alpha$) with respect to the prepreg material motion direction, and the angle ($\alpha$) varies from 45° to 90°, and
   wherein each first transversal cross line delimiting the beginning of a defective area has a first identification code, and each second transversal cross line delimiting the end of a defective area has a second identification code.

2. The defect recognition procedure in prepreg materials according to claim 1, wherein the lines are drawn with a non pollutant material that does not contain fluorine, neither polytetrafluoroetylene nor uncured silicone.

3. The defect recognition procedure in prepreg materials according to claim 2, wherein the transversal cross lines are detected by a defect detector laser sensor integrated in a manufacturing machine.

4. The defect recognition procedure in prepreg materials according to claim 3, wherein the defect detector laser measures the loss of gain between a first signal sent by the laser (preset value) and the signal that the laser receives (current value) when such first signal rebounds against the composite material.

5. The defect recognition procedure in prepreg materials according to claim 4, wherein for detecting defective areas, the comparison between the signal preset value and the signal current value determines whether or not there are defectives areas, so:
   a) if the current value is set below a certain reference, defective areas are not considered; or
   b) if the current value exceeds a certain reference, defective areas are considered and the laser control generates a signal error, stopping the machine.

6. The defect recognition procedure in prepreg materials to claim 5, wherein the first identification code and the second identification code are linked by using alphanumeric characters.

7. The defect recognition procedure in prepreg materials according to claim 5, wherein the first identification code and the second identification code are linked by using graphic characters.

8. The defect recognition procedure in prepreg materials to claim 5, wherein defective areas are not considered if the current value is set below a reference value of 30, and defective areas are considered and the laser control generates a signal error, stopping the machine if the current value exceeds a reference value of 100.

* * * * *